(12) United States Patent
Killeffer et al.

(10) Patent No.: US 9,867,970 B2
(45) Date of Patent: Jan. 16, 2018

(54) METHOD OF DEVICE ATTACHMENT TO A BIOLOGICAL SURFACE

(71) Applicant: Arkis Biosciences, Knoxville, TN (US)

(72) Inventors: James Alexander Killeffer, Knoxville, TN (US); Chad Eric Seaver, Knoxville, TN (US); Dana A. Taylor, Louisville, TN (US); James Christopher Arnott, Knoxville, TN (US)

( * ) Notice: Subject to any disclaimer, the term of this patent is extended or adjusted under 35 U.S.C. 154(b) by 380 days.

(21) Appl. No.: 14/524,578

(22) Filed: Oct. 27, 2014

(65) Prior Publication Data

US 2015/0119786 A1   Apr. 30, 2015

Related U.S. Application Data

(60) Provisional application No. 61/896,020, filed on Oct. 25, 2013.

(51) Int. Cl.
  *A61M 27/00* (2006.01)
  *A61M 25/04* (2006.01)
  *A61M 25/02* (2006.01)

(52) U.S. Cl.
  CPC .......... *A61M 27/006* (2013.01); *A61M 25/04* (2013.01); *A61M 2025/0286* (2013.01); *A61M 2209/08* (2013.01)

(58) Field of Classification Search
  CPC ................ A61M 27/006; A61M 25/04; A61M 2025/0286; A61M 2209/08
  See application file for complete search history.

(56) References Cited

U.S. PATENT DOCUMENTS

| | | | | |
|---|---|---|---|---|
| 5,722,959 | A  * | 3/1998 | Bierman | A61M 25/02 |
| | | | | 128/DIG. 26 |
| 9,295,809 | B2 * | 3/2016 | Sheetz | A61M 25/0043 |
| 2006/0224102 | A1 | 10/2006 | Glenn | |
| 2007/0060892 | A1* | 3/2007 | Propp | A61M 25/02 |
| | | | | 604/180 |
| 2007/0088391 | A1 | 4/2007 | McAlexander et al. | |

(Continued)

FOREIGN PATENT DOCUMENTS

| | | |
|---|---|---|
| EP | 2644160 | 10/2013 |
| WO | 20100128501 | 11/2010 |
| WO | 20120129391 | 9/2012 |

OTHER PUBLICATIONS

Patent Cooperation Treaty; International Search Report & Written Opinion; Form PCT/ISA/220; dated Feb. 2, 2015

(Continued)

*Primary Examiner* — Benjamin Klein
(74) *Attorney, Agent, or Firm* — Pitts & Lake, P.C.

(57) ABSTRACT

A device and means of attaching an implantable drainage lumen, catheter, or other device to an internal bodily surface, such as the peritoneum, is generally indicated by a biocompatible material or mesh fabric connected to a lumen, catheter, or other mechanical or electrical device whereby the biocompatible material or mesh may be surgically affixed to a tissue or organ by means of sutures, tacks, screws, tissue infusion or adhesion or other means in order to secure an internal drainage, or mechanical/electrical system or component for the prevention of migration or non-optimal CSF reabsorption after installation.

2 Claims, 3 Drawing Sheets

(56) References Cited

U.S. PATENT DOCUMENTS

| | | | |
|---|---|---|---|
| 2007/0198026 A1 | 8/2007 | Cauthen | |
| 2008/0262406 A1* | 10/2008 | Wiener | A61M 25/04 |
| | | | 604/8 |
| 2010/0082113 A1* | 4/2010 | Gingras | A61F 2/02 |
| | | | 623/23.72 |
| 2010/0185219 A1* | 7/2010 | Gertzman | A61L 31/005 |
| | | | 606/151 |
| 2010/0318121 A1 | 12/2010 | Levin et al. | |
| 2014/0025094 A1* | 1/2014 | Glick | A61F 2/0063 |
| | | | 606/151 |

OTHER PUBLICATIONS

European Patent Office, EPO Form 1507S—European Search Report, dated May 16, 2017.

\* cited by examiner

METHOD OF DEVICE ATTACHMENT TO A BIOLOGICAL SURFACE

CROSS-REFERENCE TO RELATED APPLICATIONS

This Application claims the benefit of U.S. Provisional Patent Application Ser. No. 61/896,020, filed Oct. 25, 2013, the contents of which are incorporated herein by reference in its entirety.

BACKGROUND OF THE INVENTION

1. Field of Invention

The present general inventive concept relates to systems and methods of treating hydrocephalus or the like, and more particularly, to ventricular or lumbar cerebral spinal fluid (CSF) shunt systems.

2. Description of the Related Art

A common contemporary treatment of hydrocephalus is to divert the flow of CSF. One strategy in obstructive hydrocephalus is to surgically pierce a hole in the bottom of the third ventricle, bypassing the obstruction. However, most commonly, CSF is diverted to a space in the body that has a large capacity to absorb it such as the peritoneum, pleura, or bloodstream. This strategy can be used with obstructive or communicating hydrocephalus and is accomplished by a device known as a shunt.

A shunt for CSF diversion typically consists of a synthetic tube placed through a hole drilled in the skull and passed through the brain into the ventricle. This is connected to a tube passed under the skin that terminates in the desired location. The shunt may be fitted with a valve designed to control pressure and flow as well as a device designed to mitigate over-drainage due to siphoning with upright posture.

Presently, in the case of hydrocephalus or other intracranial hypertension disorders, treatment utilizing a shunt for draining excess CSF between the patient's ventricles and the peritoneal cavity, or lumbar to peritoneal cavity, or ventricles to aorta artery, a drainage lumen is routed from the CSF source to a reabsorption site where a distal catheter discharges the fluid. Movement generated by the patient, or by other biological functions, can cause undesirable internal migration of the drainage system which can result in a disruption of either the collection or discharge of CSF and thereby a non-optimal reabsorption of CSF by the shunt system. Furthermore, migration of the shunt's drainage lumen(s) may interfere with other bodily functions for example in the case where drainage tubing may wrap around internal organs such as the intestines. Therefore, it is altogether desirable to affix such internal shunt components, such as drainage lumens or other shunt components, to internal organs or other areas in order to prevent undesirable migration. Such affixation may also be necessary for the securing and alignment of shunt components, such as valves, which are desired to be aligned or oriented to a gravitational field, or otherwise, with respect to patient position, so as to allow such component(s) to predictably vary its function over various patient positions while affixed. In this way, utilizing such affixation could facilitate a gravitational valve to fully compensate for CSF siphoning in the patient's standing position, for instance, while not compensating for a siphoning effect in the patient's supine position, where siphoning is of less influence to a shunt. Furthermore, such affixation may be desirable for shunt components in which ex-vivo intervention or interrogation in a particular orientation is desirable based upon an a priori knowledge of the shunt component(s) position. Such would be the case for non-invasive percutaneous programming by way of magnetic or electromagnetic means, for example, or for the case where manual manipulation by palpations is desirable.

SUMMARY OF THE INVENTION

A device and means of attaching an implantable drainage lumen, catheter, or other device to an internal bodily surface, such as the peritoneum, is generally indicated by a biocompatible material or mesh fabric connected to a lumen, catheter, or other mechanical or electrical device whereby the biocompatible material or mesh may be surgically affixed to a tissue or organ by means of sutures, tacks, screws, tissue infusion or biological growth, or adhesion or other means in order to secure an internal drainage, or mechanical/electrical system for the prevention of migration or non-optimal CSF reabsorption after installation.

The connecting fabric, flange, or other biocompatible connecting surface may be perforated or porous in order to facilitate tissue or biological growth through its material or around the material as to provide a biological attachment means to internal bodily surfaces.

The connecting fabric, flange, or other biocompatible connecting surface may also be bio-receptive as to facilitate cell growth upon itself as a further means of biologically securing a connected implantable component to the body.

In some embodiments of the present general inventive concept, a device for securely attaching a shunt to a biological structure within a patient includes a mesh to contact the shunt and having a surface interface to form an attachment with the biological structure, wherein the mesh secures the shunt in position with respect to the biological structure.

In some embodiments, the mesh supports the shunt by contacting the shunt.

In some embodiments, the mesh supports the shunt via an intermediary support structure.

In some embodiments, the mesh includes a polyester mesh.

In some embodiments, the mesh includes a polyester weave with a resorbable collagen film bonded on at least one side of the mesh.

In some embodiments, the mesh includes a self-fixating mesh.

In some embodiments, the mesh includes a collagen composite mesh.

In some embodiments, the mesh includes a biologic material selected from the group consisting of allografts, autographs, and xenographs.

In some embodiments, the mesh includes filaments.

In some embodiments, the filaments are assembled in a core/sheath construct.

In some embodiments, the filaments include monofilaments or multi-filaments.

In some embodiments, the filaments form yarns.

In some embodiments the intermediary support structure is a sleeve attached to the mesh.

In some embodiments the intermediary support structure includes a snap or button-like device to attach the shunt to the mesh.

In some embodiments, the mesh includes a plurality of openings to receive at least a portion of the shunt therein.

In some embodiments of the present general inventive concept, a method for securely attaching a shunt to a biological structure within a patient includes contacting the shunt with an attachment member, and attaching the attachment member to the biological structure, whereby the attachment member secures the shunt in position with respect to the biological structure.

In some embodiments, the attachment member includes a mesh.

In some embodiments, the mesh includes a collagen composite mesh or a self-fixating mesh.

In some embodiments, attaching the attachment member to the biological structure the mesh includes a mechanical attachment, an electrical attachment, or an attachment by tissue infusion or biological growth for temporary affixiation of the mesh to the biological structure.

In some embodiments, temporary fixture devices are used to hold the mesh in place, said temporary fixture devices selected from the group consisting of temporary screws, resorbable screws, tacks, staples, and sutures.

In some embodiments, the mesh includes a polyester weave with a resorbable collagen film bonded on at least one side of the mesh.

In some embodiments, the mesh includes filaments assembled in a core/sheath construct, the filaments including monofilaments or multi-filaments.

In some embodiments, the attaching is accomplished by a mesh, and wherein the mesh supports the shunt by securing the shunt to the biological structure.

In some embodiments, the attaching is accomplished by a mesh, and wherein a segment of the shunt is interlaced through portions of the mesh, whereby the shunt is held in position with respect to the biological structure.

In some embodiments, the attachment member is a component of an assembly, and the assembly also includes a fastening member to contact the shunt and to hold the shunt in position with respect to the biological structure.

In some embodiments, the fastening member is a sleeve, a snap fit, a button, or a button-like device.

In some embodiments of the present general inventive concept, an assembly to securely attach a shunt to a biological structure of a patient includes a mesh to support the shunt, the mesh having a surface interface to form an attachment with the biological structure to secure the shunt in position with respect to the biological structure, and a support structure interposed between the mesh and the shunt to support the shunt.

Additional features and embodiments of the present general inventive concept will be set forth in part in the description which follows and, in part, will be obvious from the description, or may be learned by practice of the present general inventive concept.

BRIEF DESCRIPTION OF THE DRAWING FIGURES

The above features, and other features and aspects of various example embodiments of the present general inventive concept, will become more apparent from examination of the drawing figures, in which.

DETAILED DESCRIPTION

Figure 1:
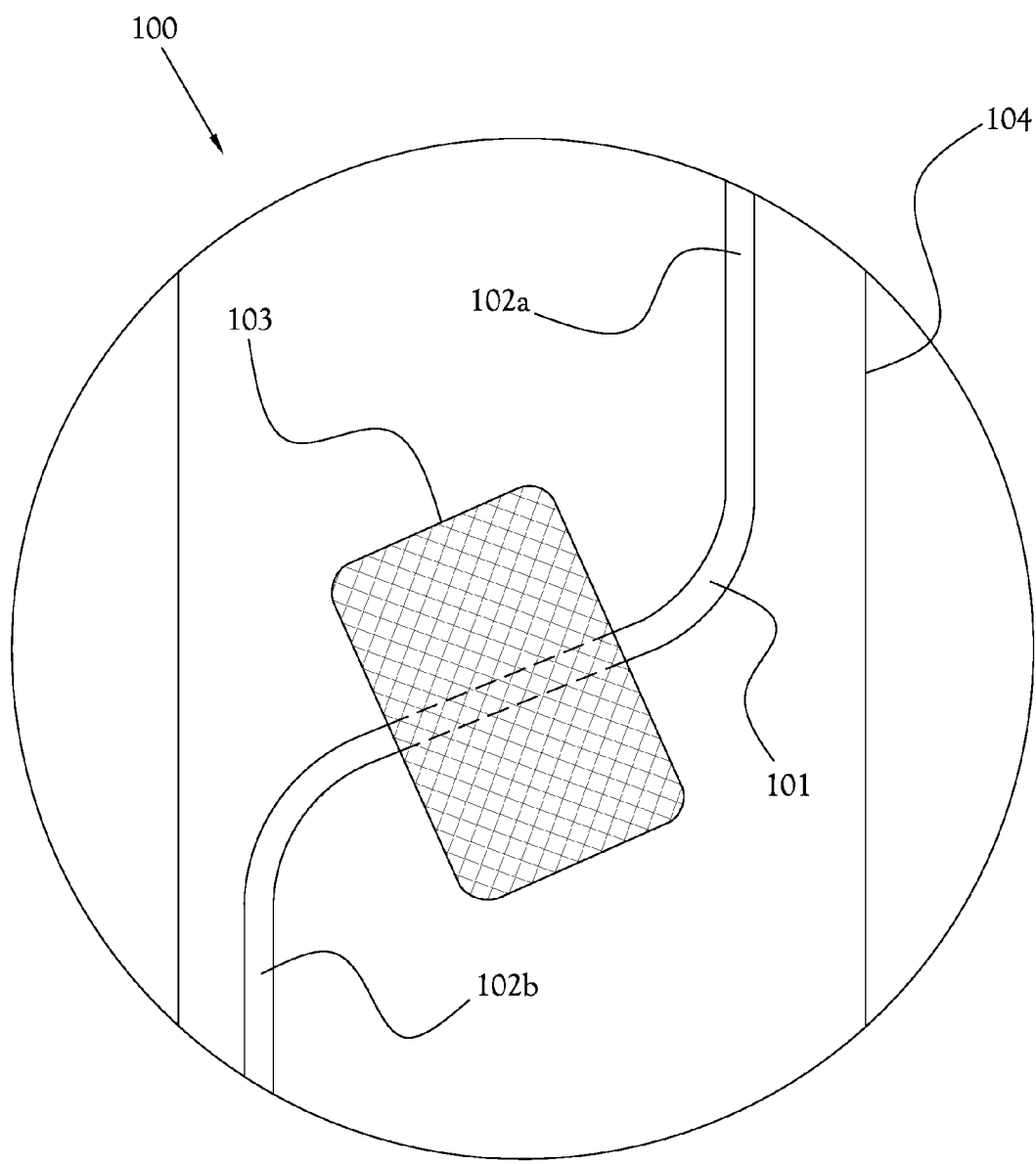
FIG. 1 illustrates a perspective view of one example embodiment of a shunt and mesh attachment device according to the present general inventive concept.

Reference will now be made to example embodiments of the present general inventive concept, examples of which are illustrated in the accompanying drawings and illustrations. The example embodiments are described herein in order to explain the present general inventive concept by referring to the figures.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The present invention includes, in some embodiments, a device for securely attaching a shunt to a biological structure within a patient including a mesh to contact the shunt and having a surface interface to form an attachment with the biological structure, wherein the mesh secures the shunt in position with respect to the biological structure. Some example embodiments of the present general inventive concept encompass methods for securely attaching a shunt to a biological structure within a patient, where such methods includes contacting the shunt with an attachment member, and attaching the attachment member to the biological structure, whereby the attachment member secures the shunt in position with respect to the biological structure.

In some embodiments of the present general inventive concept, a device for securely attaching a shunt or a shunt device to a biological structure within a patient (as, for example, during a surgical procedure) encompasses a mesh to contact the shunt or shunt device, the mesh having a surface interface to form an attachment with the biological structure, wherein the mesh secures the shunt in position with respect to the biological structure. In some embodiments, the mesh supports the shunt by directly contacting the shunt. In some embodiments, the mesh supports the shunt via an intermediary support structure (such as a polymer substrate or other substrate).

In some embodiments of the present general inventive concept, an assembly to securely attach a shunt to a biological structure of a patient includes a mesh to support the shunt, the mesh having a surface interface to form an attachment with the biological structure to secure the shunt in position with respect to the biological structure, and a support structure interposed between the mesh and the shunt to support the shunt.

With reference to FIG. 1, there is illustrated and described an internal bodily attachment mechanism. Example embodiments of the present general inventive concept can be utilized to realize a securement method of affixing components with a material such as a mesh or other biocompatible material in a hydrocephalus shunt system to internal bodily surfaces.

The invention overcomes the described limitations of the present hydrocephalus shunt system with a novel attachment mechanism that prevents unwanted movement of shunt tubing, valves, catheters, or other components. Now referring to FIG. 1, a representation of a shunt drainage lumen is illustrated as indicated by 100. The shunt drainage system 100 contains a tube or other mechanical and/or electrical component 101 with one or more entry points 102a or exit points 102b, attached or contained within a biologically compatible material attachment element 103, wherein the attachment element 103 contains a surface or other interface allowing attachment to a biologically compatible area 104 of a patient by tissue infusion, biological growth, mechanical attachment, electrical attachment, or other attachment in order to securely attach the component 101 during a surgical procedure.

Figure 2:
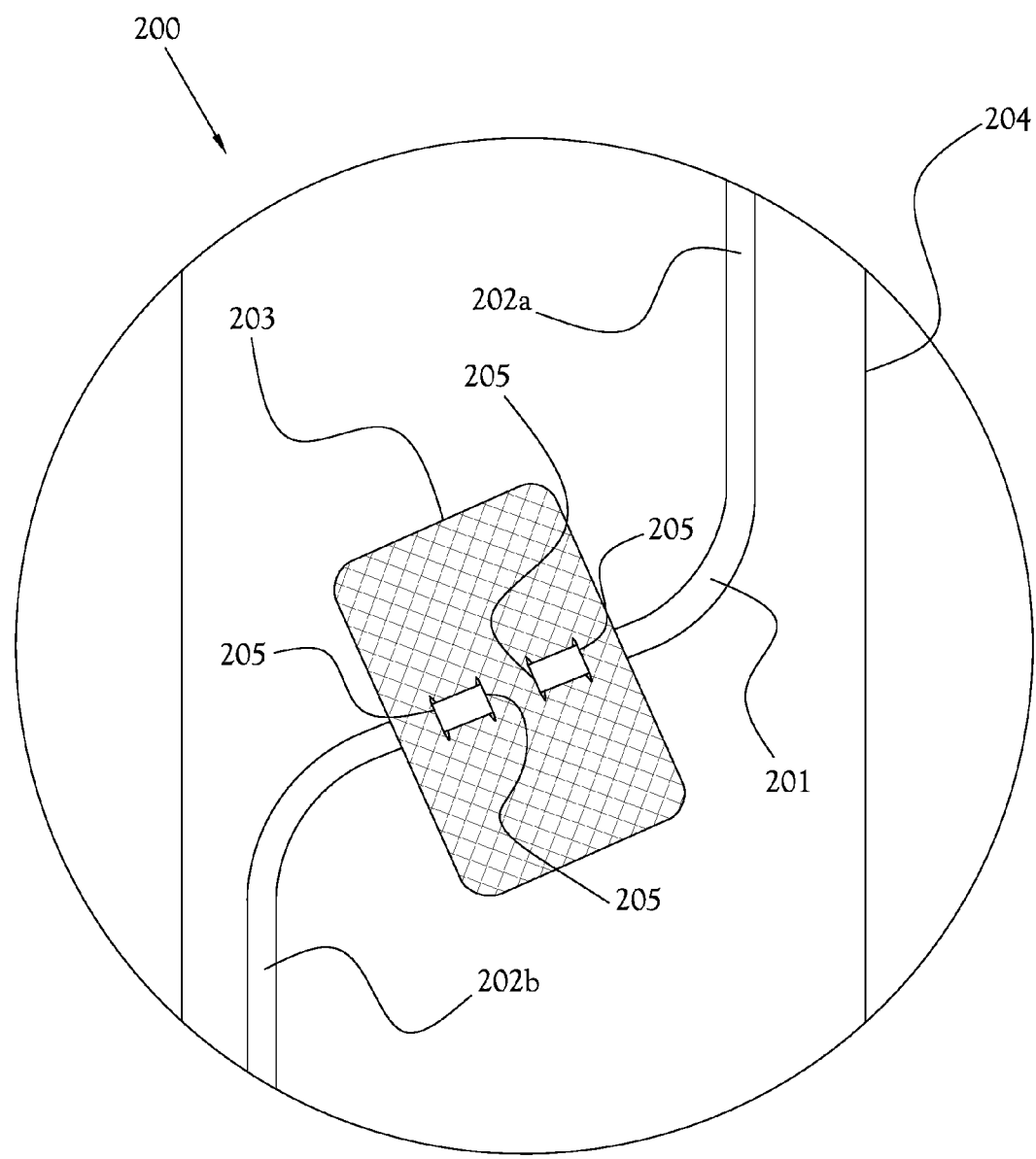
FIG. 2 illustrates a perspective view of another example embodiment of a shunt and mesh attachment device according to the present general inventive concept.

Another example embodiment of a shunt drainage system assembly is illustrated generally in FIG. 2. As shown in FIG. 2, the shunt drainage system 200 includes a tube or other mechanical and/or electrical component 201 (hereinafter "shunt device tube," as illustrated in FIG. 2 by way of example) with one or more entry points 202a or exit points 202b, held in place with respect to a biologically compatible area 204 of a patient by a mesh attachment element 203. In the illustrated example embodiment, the shunt device tube 201 is interlaced through the mesh attachment element 203, with a segment of the shunt device tube 201 threaded through apertures 205 in the mesh attachment element 203, so that the shunt device tube 201 passes over and under, repeatedly, portions of the mesh attachment element 203. In this way, the mesh attachment element 203 holds the shunt device tube 201 in place with respect to the biologically compatible area 204 of the patient. As with the example embodiment illustrated in FIG. 1, the attachment element 203 illustrated generally in FIG. 2 generally includes a surface or other interface allowing attachment to the biologically compatible area 204 of the patient by tissue infusion, biological growth, mechanical attachment, electrical attachment, or other attachment.

Figure 3:
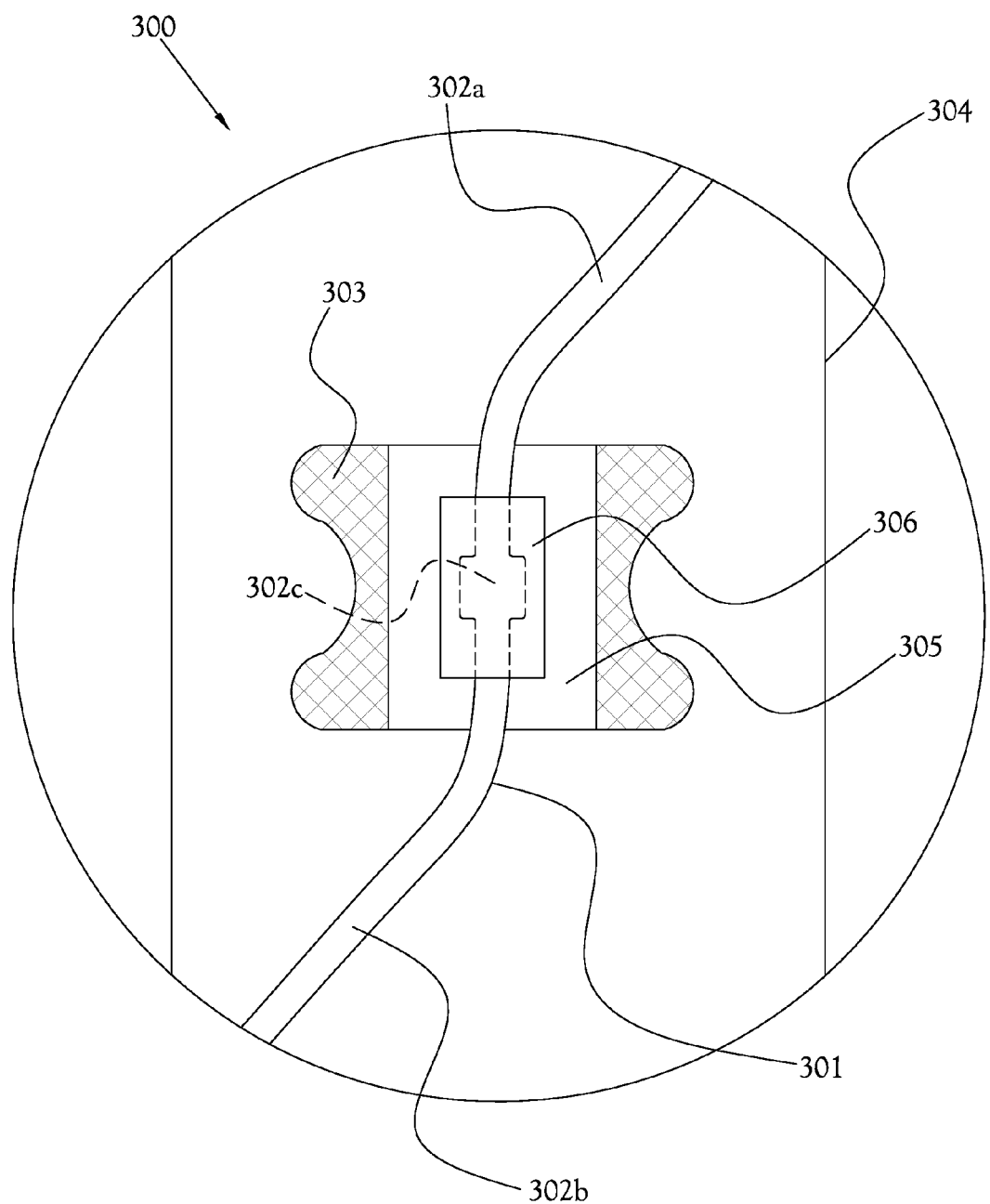
FIG. 3 illustrates a perspective view of another example embodiment of a shunt and mesh attachment device according to the present general inventive concept.

Now referring to FIG. 3, a representation of a shunt drainage lumen is illustrated as indicated by 300. The shunt drainage system assembly 300 includes a tube or other mechanical and/or electrical component 301 (hereinafter "shunt device") with one or more entry points 302a or exit points 302b and/or component(s) 302c, such as a valve, reservoir, or other shunt component. A mesh or other attachment element 303 contains a surface interface or other interface allowing attachment of the assembly 300 to a biologically compatible area 304 of a patient by tissue infusion, biological growth, mechanical, electrical, or other attachment means. In the illustrated example embodiment, an intermediary member 305 is interposed between the shunt device 301 and the attachment element 303; in some embodiments, the intermediary member 305 includes a polymer substrate or some other substrate. In some embodiments, such as that illustrated in FIG. 3, the assembly 300 also includes a fastening member or securing member 306 to secure the shunt device 301 to the intermediary member 305. In some example embodiments, the fastening member or securing member includes a sleeve. In some example embodiments, the fastening member or securing member includes a tight-fit sleeve, or a sleeve with tight-fitting ends that fit snugly around the shunt device. In some example embodiments, the fastening member or securing member includes a snap fit, a button, a button-like device, or some similar securing device.

Suitable meshes for use in various example embodiments of the present general inventive concept include, by way of example, a collagen composite mesh such as PARIETEX™ Composite Mesh (commercially available from Tyco Healthcare Group LP, d/b/a Covidien). PARIETEX™ Composite Mesh is a 3-dimensional polyester weave with a resorbable collagen film bonded on one side. Another suitable mesh includes PARIATEX PROGRIP™ self-fixating mesh (also commercially available from Covidien). PARIATEX PROGRIP™ is a polyester mesh, which includes poly lactic acid (PLA) grip members. Other suitable meshes include those sold under the names PARIETENE®, PARIETEX™, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); PROLITE™, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT® mesh (all commercially available from W.L. Gore).

Additionally, meshes within the scope and context of the present general inventive concept include biologic materials such as allografts (i.e., ALLODERM® Regenerative Tissue Matrix from Lifecell), autografts, and xenografts (i.e., PERMACOL™, from Covidien). In alternate embodiments, processed/purified tissues may also be employed or other such biocompatible materials comprising an affixation means.

In certain embodiments, PARIATEX™ Composite Mesh or PARIATEX PROGRIP™ may be utilized in accordance with the present invention.

In some embodiments, the mesh includes filaments such as monofilaments or multi-filaments. In some embodiments, a plurality of multi-filaments are combined to form yarns. It is envisioned that the mesh may be configured to any size and/or shape suitable for shunt positioning. Further, in some embodiments, the filaments include core/sheath constructs.

In some embodiments, temporary fixture devices or means, such as temporary screws, resorbable screws, tacks, staples, or sutures, are used to hold the mesh or other interface surface or attachment member in place in order to allow time for biological "in-growth" or merging of the mesh or other interface surface or attachment member with the biological structure.

In some embodiments, multiple, separate meshes or attachment elements are used to secure a single shunt device.

The above described attachment method can also be applied to non-mesh attachable devices for securing more solid incased medical devices such as titanium encased implantable medical devices designed with mesh attachment points covering at least some portion of the solid medical implant encasement.

The medical devices described herein may be formed using any method within the purview of those skilled in the art. Some non-limiting examples include, weaving, knitting, braiding, crocheting, extruding, spraying, casting, molding, and combinations thereof. In embodiments, the medical device may include a two or three-dimensional surgical mesh which is woven, knitted, braided, or crocheted.

As explained by the foregoing, disclosed herein are devices and means of attaching an implantable drainage lumen, catheter, or other device to an internal bodily surface, such as the peritoneum, and is generally indicated by a biocompatible material or mesh fabric connected to a lumen, catheter, or other mechanical or electrical device whereby the biocompatible material or mesh may be surgically affixed to a tissue or organ by means of sutures, tacks, screws, tissue infusion and/or biological growth, or adhesion or other means in order to secure an internal drainage, or mechanical/electrical system for the prevention of migration or non-optimal CSF reabsorption after installation.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A device to securely attach a shunt to a biological structure of a patient, comprising:

a shunt to divert bodily fluid in a patient from a first area to a second area;

a mesh to support the shunt, the mesh having a top surface and an opposing surface interface, the surface interface being configured to form an attachment with a biological structure to secure the shunt in position with respect to the biological structure; and a plurality of apertures formed in the mesh to receive the shunt in an interlaced formation such that the shunt passes over the top surface and under the surface interface as the shunt enters and exits respective apertures, wherein the mesh comprises a polyester weave with a resorbable collagen film bonded on at least one side of the mesh.

2. A device to securely attach a shunt to a biological structure of a patient, comprising:

a shunt to divert bodily fluid in a patient from a first area to a second area;

a mesh to support the shunt, the mesh having a top surface and an opposing surface interface, the surface interface being configured to form an attachment with a biological structure to secure the shunt in position with respect to the biological structure; and a plurality of apertures formed in the mesh to receive the shunt in an interlaced formation such that the shunt passes over the top surface and under the surface interface as the shunt enters and exits respective apertures, wherein the mesh comprises a biologic material selected from the group consisting of allografts, autographs, and xenographs.

* * * * *